United States Patent [19]
Bolich, Jr. et al.

[11] 4,206,195
[45] Jun. 3, 1980

[54] HAIR CONDITIONING ARTICLE AND A METHOD OF ITS USE

[75] Inventors: Raymond E. Bolich, Jr., Maineville; David N. DiGiulio, Cincinnati, both of Ohio

[73] Assignee: The Procter & Gamble Company, Cincinnati, Ohio

[21] Appl. No.: 41,655

[22] Filed: May 23, 1979

Related U.S. Application Data

[63] Continuation-in-part of Ser. No. 913,139, Jun. 6, 1978.

[51] Int. Cl.$^2$ .................. A61K 7/06; A61K 7/08; A61K 7/11
[52] U.S. Cl. .................. 424/16; 424/25; 424/28; 424/70; 424/71; 132/9; 79 A; 132/79 D; 132/88.7; 132/DIG. 3; 15/104.93; 15/104.94; 15/209 R
[58] Field of Search .................. 424/16, 25, 28, 70, 424/71; 132/9, 79 A, 79 D, 88.7, DIG. 3; 15/104.93, 104.94, 209 R

[56] References Cited

U.S. PATENT DOCUMENTS

| 711,263 | 10/1902 | Robertson | 424/70 |
|---|---|---|---|
| 2,154,822 | 4/1939 | Quisling | 107/88 |
| 2,437,298 | 3/1948 | Heyman | 132/27 |
| 2,665,528 | 1/1954 | Sternfield | 15/104.93 |
| 2,837,099 | 6/1958 | Van Meer | 132/110 |
| 3,088,469 | 5/1963 | Berryhill et al. | 132/9 |
| 3,155,591 | 11/1964 | Hilfer | 424/70 |
| 3,164,481 | 1/1965 | Shibe | 106/10 |
| 3,579,632 | 5/1971 | Sonnen | 424/70 |
| 3,580,853 | 5/1971 | Parran | 252/152 |
| 3,632,396 | 1/1972 | Perez-Zamura | 117/76 P |
| 3,676,199 | 7/1972 | Hewitt et al. | 117/109 |
| 3,686,025 | 8/1972 | Morton | 117/140 R |
| 3,696,034 | 10/1972 | Hewitt et al. | 252/8.8 |
| 3,895,128 | 7/1975 | Gaiser | 428/43 |
| 3,944,694 | 3/1976 | McQueary | 428/131 |
| 3,954,113 | 5/1976 | Bohrer | 132/7 |
| 3,956,556 | 5/1976 | McQueary | 428/131 |
| 3,992,336 | 11/1976 | Faucher | 260/17 R |
| 4,013,086 | 3/1977 | Chmela | 132/110 |
| 4,076,633 | 2/1978 | Edwards et al. | 252/8.75 |
| 4,149,551 | 4/1979 | Benjamin et al. | 132/7 |

Primary Examiner—Shep K. Rose
Attorney, Agent, or Firm—Douglas C. Mohl; John V. Gorman; Richard C. Witte

[57] ABSTRACT

An article especially designed for conditioning hair comprising a flexible substrate releasably carrying a hair conditioning agent and a water soluble salt. The article when rubbed onto hair provides combing, detangling, static fly-away and softness benefits. Additionally the manageability of the hair is improved.

18 Claims, No Drawings

HAIR CONDITIONING ARTICLE AND A METHOD OF ITS USE

CROSS-REFERENCE TO RELATED APPLICATION

This is a continuation-in-part of our copending application Ser. No. 913,139 filed June 6, 1978.

TECHNICAL FIELD

The subject invention relates to a hair conditioning article and the method of its use. More particularly, the article comprises a flexible substrate releasably carrying a hair conditioning agent and a water soluble salt. In its method aspect, the subject invention relates to the use of the article to condition hair, preferably after shampooing but prior to completely drying.

BACKGROUND ART

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. A variety of approaches have been developed to alleviate the aftershampoo problems. These range from the inclusion of hair conditioning aids in shampoos to post-shampoo application of hair conditioners, i.e. hair rinses. Difficulties associated with the use of conditioning aids in shampoos have been compatibility problems and a greasy feel on the just-washed hair. Hair rinses typically work by depositing a polymeric film or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient. The results obtained in this manner also have not been fully satisfactory due to the difficulties associated with the deposition and retention on the hair of the hair conditioning aid.

Attempts have been made to alleviate some of the above problems by use of a substrate article to condition hair. Such attempts have not proven to be entirely successful. The lack of success has been related to poor transfer of the hair conditioning agent from the substrate to the hair, unsatisfactory wet hair feel and the lack of sufficient dry hair manageability benefits. The problem is inefficient transfer of an active from a substrate to a surface has been faced previously in the dryer added fabric conditioning field. See for example U.S. Pat. No. 3,743,534, July 3, 1973 to Zamora wherein release is improved by coating the substrate first with a solid waxy material. See also U.S. Pat. No. 3,944,694, Mar. 16, 1976 to McQueary wherein the substrate is first coated with paraffin.

Although the above references disclose methods of improving conditioner release in the fabric conditioning field, the references do not suggest methods for improving wet hair feel and dry hair manageability.

Many different materials have been applied to fabrics from a substrate particularly in the clothes dryer context to improve the treated material's properties. Included among prior art references are U.S. Pat. No. 4,076,633, Feb. 28, 1978 to Edwards et al and U.S. Pat. No. 4,073,996, Feb. 14, 1978 to Bedenk et al. The Edwards et al patent describes articles containing starch particles while the Bedenk et al patent describes articles containing particles of smectite clay. While these methods have been disclosed, there is no suggestion to use them on hair. Furthermore, there is no suggestion to use water soluble salts on a substrate for conditioning fabrics, even less hair.

It is an object of the present invention to provide a superior article for use in conditioning hair.

It is a further object of the present invention to provide a superior hair conditioning article comprising a flexible substrate releasably carrying a hair conditioning agent and a water soluble salt.

A still further object of the present invention is to provide a superior method for conditioning hair.

These and other objects of the invention will become apparent from the description to follow.

As used herein, all percents and ratios are by weight unless otherwise indicated.

DISCLOSURE OF INVENTION

An article for conditioning hair to provide combing, detangling, static fly-away, softness and manageability benefits comprising a flexible substrate releasably carrying from about 1.5 grams to about 20.0 grams per square meter of substrate of a normally solid hair conditioning agent and from about 0.3 to about 15.0 grams per square meter of substrate of a water soluble salt or mixtures of salts. The method described herein relates to rubbing the hair to be treated with the above described article thereby transfering an effective amount of hair conditioning agent to the hair.

DETAILED DESCRIPTION OF THE INVENTION

The hair conditioning agent may be present as a first (bottom) coating on the substrate, blended together with the water soluble salt or present as the second (top) coating over a coating of the water soluble salt. Preferably, the articles herein have the hair conditioning agent present as a second (top) coating. The stated position herein of the hair conditioning agent and the water soluble salt are relative to one another and do not involve other materials which may be present on the substrate.

The article of this invention comprises a flexible substrate releasably carrying a normally solid hair conditioning agent and a water soluble salt. Although the term "coating" is used herein it is to be recognized that impregnation of the substrate by the hair conditioning agent also takes place. Rubbing of the hair with the article, the method aspect of this invention, transfers the hair conditioning agent and the water soluble salt from the flexible substrate to the hair. The article herein provides convenience as well as performance benefits, i.e. combing, detangling, static fly-away, softness, and manageability. A detailed description of the various essential components of the article and method is contained in the succeeding paragraphs.

Flexible Substrate

The flexible substrate of the present articles include a variety of natural or synthetic materials. Included are those which have the ability to retain the hair-conditioning agent in a form which is releasable to hair rubbed therewith and which have a resistance to shredding or tearing. Examples of suitable substrates include paper towelling, swatches or woven and non-woven cloth, papers, sponges, plastics and felts. Fibrous materials can be natural or synthetic but are preferably cellulosic. Foam plastic materials, such as the polyurethanes can also be employed.

In one embodiment of the present invention a substrate which is relatively impermeable to the hair conditioning agent is used. Included among such impermeable substrates are waxy papers or woven or nonwoven cloths which carry coatings of paraffin or microcrystalline or synthetic wax. When used such materials are present at a level of from about 0.3 gram to 15.0 grams, preferably about 1.5 grams to 6.0 grams, per square meter of substrate.

Preferred open or porous substrates of a paper, woven cloth or nonwoven cloth nature useful herein are fully disclosed in U.S. Pat. no. 3,686,025, Morton, TEXTILE SOFTENING AGENTS IMPREGNATED INTO ABSORBENT MATERIALS, issued Aug. 22, 1972, incorporated herein by reference. These substrates are considered to be absorbent; the term "absorbent", as used herein, is intended to mean a substance with an absorbent capacity (i.e., a parameter representing a substrate's ability to take up and retain a liquid) from 5.5 to 12, preferably 7 to 10, times its weight of water.

The preferred substrates used in this invention can also be defined in terms of "free space". Free space, also called "void volume", as used herein is intended to mean that space within a structure that is unoccupied. For example, certain multiply paper structures comprise plies embossed with protuberances, the ends of which are mated and joined; this paper structure has a void volume or free space between the fibers of the paper sheet itself. A nonwoven cloth also has free space between each of its fibers. The free space of nonwoven cloth or paper, having designated physical dimensions, can be varied by modifying the density of the paper of nonwoven cloth. Substrates with a high amount of free space generally have low fiber density; high density substrates generally have a low amount of free space.

A suitable paper substrate comprises a compressible, laminated, calendered, multiply, absorbent paper structure. Preferably, the paper structure has 2 or 3 plies and a total basis weight of from 20 to 140 grams per square meter and absorbent capacity values within the range of 7 to 10. Each ply of the preferred paper structure has a basis weight of about 3 to 13 kilograms per 280 square meters, and the paper structure can consist of plies having the same or different basis weights. Each ply is preferably made from a creped, or otherwise extensible, paper with a creped percentage of about 15% to 40% and a machine direction (MD) tensile and crossmachine (CD) tensile of from about 15 to 230 grams per square cm of paper width. The two outer plies of a 3-ply paper structure or each ply of a 2-ply paper structure are embossed with identical repeating patterns consisting of about 2.5 to 30 discrete protuberances per square cm, raised to a height of from about 0.25 cm to 1 cm above the surface of the unembossed paper sheet. From about 10% to 60% of the paper sheet surface is raised. The distal ends (i.e. the ends away from the unembossed paper sheet surface) of the protuberances on each ply are mated and adhesively joined together, thereby providing a preferred paper structure exhibiting a compressive modulus of from about 31 to 120 cm grams per cubic cm and Handle-O-Meter (HOM) MD and CD values of from about 10 to 130.

Suitable adhesives for multiply paper are known in the art and include water, starches, wet strength resins, and polyvinyl acetates. A particularly suitable adhesive is prepared by heating from about 2 to about 4 parts by weight of substantially completely hydrolyzed polyvinyl alcohol resin in from about 96 to about 98 parts by weight of water. Preferably, about 0.04 grams of adhesive solids are used to join a square meter of the embossed plies, with the adhesive being applied to the distal surfaces of the protuberances of one or all plies.

The compressive modulus values which define the compressive deformation characteristics of a paper structure compressively loaded on its opposing surfaces, the HOM values which refer to the stiffness or handle of a paper structure, the MD and CD HOM values which refer to HOM values obtained from paper structure samples tested in machine and crossmachine direction, the methods of determining these values, the equipment used, and a more detailed disclosure of the paper structure preferred herein, as well as methods of its preparation, can be found in U.S. Pat. No. 3,414,459, Wells, COMPRESSIBLE LAMINATED PAPER STRUCTURE, issued Dec. 3, 1968, the disclosures of which are incorporated herein by reference.

The preferred nonwoven cloth substrates used in the invention herein are generally defined as adhesively bonded fibrous or filamentous products having a web or carded fiber structure (where the fiber strength is suitable to allow carding), or comprising fibrous mats in which the fibers or filaments are distributed haphazardly or in random array (i.e., an array of fibers in a carded web wherein partial orientation of the fibers is frequently present, as well as a completely haphazard distributional orientation), or substantially aligned. The fibers or filaments can be natural (e.g., wool, silk, jute, hemp, cotton, linen, sisal, or ramie) or synthetic (e.g., rayon, cellulose ester, polyvinyl derivatives, polyyolefins, polyamides, or polyesters).

Methods of making nonwoven cloths are not a part of this invention and, being well known in the art, are not described in detail herein. Generally, such cloths are made by air or waterpaying processes in which the fibers or filaments are first cut to desired lengths from long strands, passed into a water or air stream, and then deposited onto a screen through which the fiberladen air or water is passed. The deposited fibers or filaments are then adhesively bonded together, dried, cured, and otherwise treated as desired to form the nonwoven cloth. Nonwoven cloths made of polyesters, polyamides, vinyl resins, and other thermoplastic fibers can be spunbonded, i.e., the fibers are spun out onto a flat surface and bonded (melted) together by heat or by chemical reactions.

The absorbent properties required with nonwoven cloths are provided merely by building up the thickness of the cloth, i.e. by superimposing a plurality of carded webs or mats to a thickness adequate to obtain the necessary absorbent properties, or by allowing a sufficient thickness of the fibers to deposit on the screen. Any diameter or denier of the fiber (generally up to about 10 denier) can be used, inasmuch as it is the free space between each fiber that makes the thickness of the cloth directly related to the absorbent capacity of the cloth, and which, further, makes the nonwoven cloth especially suitable for coating with a hair conditioning agent by means of intersectional or capillary action. Thus, any thickness necessary to obtain the required absorbent capacity can be used.

The choice of binder-resins used in the manufacture of nonwoven cloths provides substrates possessing a variety of desirable traits. For example, the absorbent capacity of the cloth is increased, decreased or regulated by respectively using a hydrophilic binder resin, a hydrophobic binder resin, or a mixture thereof, in the fiber bonding step.

When the substrate for the articles herein is a nonwoven cloth made from fibers deposited haphazardly or in random array on the screen, the articles exhibit excellent strength in all directions and are not prone to tear or separate when used in the hair conditioning method.

The preferred nonwoven cloth is waterlaid or airlaid and is made from cellulosic fibers, particularly from regenerated cellulose, polyester or polyolefin, which are lubricated with any standard textile lubricant. Preferably, the fibers are from 0.45 cm to 5 cm in length and are from 1.5 to 5 denier. Preferably, the fibers are at least partially oriented haphazardly, particularly substantially haphazardly, and are adhesively bonded together with a hydrophobic or substantially hydrophobic binder-resin, particularly with a nonionic self-cross-linking acrylic polymer or polymers. Preferably, the cloth comprises about 70% fiber and 30% binder-resin polymer by weight and has a basis weight of from 20 to 80 grams per square meter.

Woven cloths are the single or double knit cloths made from natural fibers, (e.g. cotton or wool) synthetic fibers (e.g. rayon, polypropylene or polyester) or fiber blends (e.g. a cotton/polyester blend). Such cloths have a basis weight of from 20 to 140 grams per square meter.

Hair Conditioning Agent

The hair conditioning agent associated with the above described flexible substrate is normally solid, i.e. solid at temperatures below 25° C. compound. It can be selected from any of a wide variety of cationic, nonionic, anionic, zwitterionic and ampholytic agents and mixtures thereof. The cationic agents, particularly the quanternary ammonium salts are preferred. In addition to their combing, detangling, softness, luster and manageability benefits, they provide excellent static fly-away benefits. The individual classes of hair conditioning agents are discussed in the following paragraphs.

Quaternary ammonium salts have the formula:

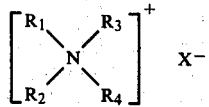

wherein $R_1$ is hydrogen, an aliphatic group of from 1 to 22 carbon atoms, or aromatic, aryl or alkaryl groups having from 12 to 22 carbon atoms; $R_2$ is an aliphatic group having 1-22 carbon atoms; $R_3$ and $R_4$ are each alkyl groups of from 1 to 3 carbon atoms, and X is an anion selected from halogen, acetate, phosphate, nitrate and methyl sulfate radicals. The aliphatic groups may contain, in addition to carbon and hydrogen atoms, ether linkages as well as amido groups among other groups.

Preferred quaternary ammonium salts are the dialkyl dimethyl ammonium chlorides, wherein the alkyl groups have from 12 to 22 carbon atoms and are derived from long-chain fatty acids, such as hydrogenated tallow. The term "tallow" refers to fatty alkyl groups derived from tallow fatty acids. Such fatty acids give rise to quaternary ammonium compounds wherein $R_1$ and $R_2$ have predominately from 16 to 18 carbon atoms. The term "coconut" refers to fatty acid groups from coconut oil fatty acids. The coconut-alkyl $R_1$ and $R_2$ groups have from about 8 to about 18 carbon atoms and predomonate in $C_{12}$ to $C_{14}$ alkyl groups.

Representative examples of quaternary ammonium salts of the invention include ditallow dimethyl ammonium chloride; ditallow dimethyl ammonium methyl sulfate; dihexadecyl dimethyl ammonium chloride; di(-hydrogenated tallow) dimethyl ammonium chloride; dioctadecyl dimethyl ammonium chloride; dieicosyl dimethyl ammonium chloride; didocosyl dimethyl ammonium chloride; di(hydrogenated tallow) dimethyl ammonium acetate; dihexadecyl diethyl ammonium chloride; dihexadecyl dimethyl ammonium acetate; ditallow dipropyl ammonium phosphate; ditallow dimethyl ammonium nitrate; di(coconutalkyl)dimethyl ammonium chloride; and stearyl dimethyl benzyl ammonium chloride.

Other quaternary ammonium salts useful herein are the compounds of the formula

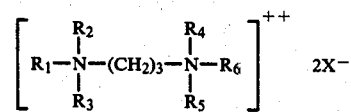

wherein $R_1$ is an aliphatic group having 16 to 22 carbon atoms, $R_2$, $R_3$, $R_4$, $R_5$ and $R_6$ are the same or different and are selected from H and alkyls having 1-4 carbon atoms and X is an anion as above defined. Tallow propanediammonium dichloride is an example of this quaternary ammonium salt.

Quaternary imidazolinium salts have the formula

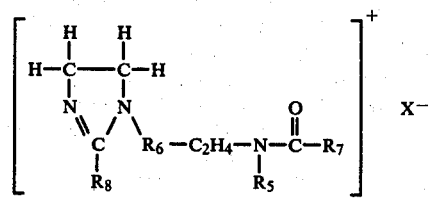

wherein $R_6$ is an alkyl group containing from 1 to 4, preferably from 1 to 2 carbon atoms, $R_5$ is an alkyl group containing from 1 to 4 carbon atoms or a hydrogen radical, $R_8$ is an alkyl group containing from 1 to 22, preferably at least 15 carbon atoms, or a hydrogen radical $R_7$ is an alkyl group containing from 8 to 22, preferably at least 15 carbon atoms and X is an anion, preferably chloride. Other suitable anions include those disclosed with reference to the quaternary ammonium salts described hereinbefore.

Particularly preferred are those imidazolinium salts in which both $R_7$ and $R_8$ are alkyl of from 12 to 22 carbon atoms, e.g., 1-methyl-1-[(stearoylamide)ethyl]-2-heptadecyl-4, 5-dihydroimidazolinium chloride; 1-methyl-1-[(palmitoylamide)ethyl]-2-octadecyl-4,5-dihydroimidazolinium chloride and 1-methyl-1-[(tallowamide)ethyl]-2-tallowimidazolinium methyl sulfate.

Included as a suitable hair conditioner herein are fatty amines. As used herein they may be primary, secondary or tertiary but the alkyl, substituted and unsubstituted groups preferably have from 12–22 carbon atoms. Preferred are the primary and secondary amines with the primary being the most preferred. Diamines having a long chain alkyl group may also be used. Examples of amines suitable for use include dimethyl stearamine, dimethyl soyamine, stearylamine, soyamine, myristyl amine, tridecylamine, ethyl stearylamine, N-tallow propanediamine, ethoxylated (5 moles E.O.) stearylamine dihydroxyethyl stearylamine and arachidylbehenylamine.

Salts of the above described amines are also suitable for use herein. The anions of such salts include those mentioned previously for the quaternary ammonium salts. Specific amine salts include stearylamine hydrochloride, soyamine chloride, stearylamine formate and N-tallow propanediamine dichloride.

The nonionic agents useful herein include many of a wide variety of materials. Included are sorbitan esters, fatty alcohols, polyhydric alcohol esters, tertiary phosphine oxides, tertiary amine oxides and ethoxylated alcohols among many others.

The sorbitan esters are the esterified cyclic dehydration products of sorbitol, i.e., sorbitan ester. Sorbitol, itself prepared by catalytic hydrogenation of glucose, is dehydrated in well known fashion to form mixtures of cyclic, 1,4- and 3,6-sorbitol anhydrides and small amounts of isosorbides. (See Brown; U.S. Pat. No. 2,322,821; issued June 29, 1943.) The resulting complex mixtures of cyclic anhydrides of sorbitol are collectively referred to herein as "sorbitan". It will be recognized that this "sorbitan" mixture will also contain some free uncyclized sorbitol.

Sorbitan esters useful herein are prepared by esterifying the "sorbitan" mixture with a fatty acyl group in standard fashion, e.g., by reaction with a fatty ($C_{10}$–$C_{24}$) acid or fatty acid halide. The esterification reaction can occur at any of the available hydroxyl groups, and various mono-, di-, etc., esters can be prepared. In fact, complex mixtures of mono-, di-, tri-, and tetra-esters almost always result from such reactions, and the stoichiometric ratios of the reactants can simply by adjusted to favor the desired reaction product.

The foregoing complex mixtures of esterified cyclic dehydration products or sorbitol (and small amounts of esterified sorbitol) are collectively referred to herein as "sorbitan esters". Sorbitan mono- and di-esters of lauric, myristic, palmitic, stearic and behenic acids are particularly useful herein. Mixed sorbitan esters, e.g. mixtures of the foregoing esters, and mixtures prepared by esterifying sorbitan with fatty acid mixtures such as the mixed tallow and hydrogenated palm oil fatty acids, are useful herein and are economically attractive. Unsaturated $C_{10}$–$C_{18}$ sorbitan esters, e.g., sorbitan mono-oleate, usually are present in such mixtures. It is to be recognized that all sorbitan esters, and mixtures thereof, which are essentially water-insoluble and which have fatty hydrocarbyl "tails", are materials in the context of the present invention.

The preferred alkyl sorbitan ester materials herein comprise sorbitan monomyristate, sorbitan monopalmitate, sorbitan monostearate, sorbitan monobehenate, sorbitan dilaurate, sorbitan dimyristate, sorbitan dipalmitate, sorbitan distearate, sorbitan dibehenate, and mixtures thereof, the mixed coconutalkyl sorbitan mono- and di-esters and the mixed tallow-alkyl sorbitan mono- and di-esters. The tri- and tetra-esters of sorbitan and lauric, myristic, palmitic, stearic and behenic acids, and mixtures thereof, are also useful herein.

Another useful type of hair conditioning agent is the substantially water-insoluble compounds chemically classified as fatty alcohols. Mono-ols, di-ols, and poly-ols having the requisite melting point properties set forth above are useful herein.

A preferred type of alcohol useful herein includes the higher melting members of the so-called fatty alcohol class. Although once limited to alcohols obtained from natural fats and oils, the term "fatty alcohols" has come to mean those alcohols which correspond to the alcohols obtainable from fats and oils, and all such alcohols can be made by synthetic processes. Fatty alcohols prepared by the mild oxidation of petroleum products are useful herein. Preferred fatty alcohols are saturated and have from 14 to 18 carbon atoms.

Examples of satisfactory alcohols are 1-tricosanol, 1-tetradecanol, 1-hexadecanol, 1-heptadecanol, 1-octadecanol, 1-eicosanol, 15-methyl hexadecanol, 1-heneicosanol, 2-octadecanol, 2-eicosanol, 1,1-diphenyl hexadecanol, 4-methylbenzyl alcohol, 1,12-octadecanediol, and 1,10-decanediol.

Another type of hair conditioning agent useful in the instant invention encompasses various esters of polyhydric alcohols. Polyhydric alcohols (e.g. glycerol, pentaerythritol and ethylene glycol) are reacted with a fatty acid containing 8 to 20 carbon atoms in wellknown fashion to produce the polyhydric alcohol esters. Such compounds can be fully esterified or can have one or more free hydroxyl groups provided they have a melting point within the range recited herein and are substantially water-insoluble.

Esters of glycerol useful herein include the mono-, di- and tri-glycerides. The fatty acid groups on the glycerides contain from 8 to 20 carbon atoms. In particular, di-glycerides containing two $C_8$–$C_{20}$, preferably $C_{10}$–$C_{18}$, alkyl groups in the molecule are useful hair conditioning agents.

Non-limiting examples of polyhydric alcohol esters useful herein include: glycerol-1,2-dilaurate; glycerol-1,3-dilaurate; glycerol-1,2-dimyristate; glycerol-1,3-dimyristate; glycerol-1,2-dipalmitate; glycerol-1,3-dipalmitate; glycerol-1,2-distearate; glycerol-1,3-distearate; glycerol-1,2,3-trimyristate; butane tetraol-1,2,3-tristearate; ethylene glycol monostearate; and ethylene glycol distearate. Mixed glycerides available from mixed tallowalkyl fatty acids, i.e., 1,2-ditallowalkyl glycerol, 1,3-ditallowalkyl glycerol, and 1,2,3-tri-tallowalkyl glycerol are economically attractive for use herein. The foregoing esters are preferred for use herein due to their ready availability from natural fats and oils.

Tertiary phosphine oxides are also suitable for use in the articles described herein. These compounds have the generic formula

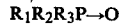

$R_1R_2R_3P \rightarrow O$ wherein $R_1$ is alkyl, alkenyl or monohydroxyalkyl having a chain length of from 20 to 30 carbon atoms and wherein $R_2$ and $R_3$ are each alkyl or monohydroxyalkyl containing from 1 to 4 carbon atoms. Specific examples include eicosyldimethylphosphine oxide, docosyldiethylphosphine oxide and hexacosyldimethylphosphine oxide.

Tertiary amine oxides suitable for use herein are similar to the phosphine oxides in terms of the alkyl groups. These compounds have the generic formula $$R_1R_2R_3N \rightarrow O$$

wherein $R_1$ $R_2$ and $R_3$ are as described above. Specific examples include docosyldimethylamine oxide, docosyl-bis-(b-hydroxyethyl)amine oxide and tricosyldiethylamine oxide.

The anionic agents include salts of fatty acids, alkyl sulfates, alkyl sulfonates and ethoxylated alkyl sulfates. The alkyl groups in these agents can contain from about 8 to 20 carbon atoms.

Fatty acids salts, especially the salts of the fatty acids having from 8 to 20 carbon atoms are used herein. Such salts are prepared by neutralizing the free fatty acids with a metallo base, e.g. $Mg(OH)_2$ or $Ca(OH)_2$ in well known fashion.

Examples of suitable fatty acid salts include calcium dodecanate, calcium tetradecanate, aluminum hexadecanate, magnesium hexadecanate, calcium eicosate, calcium 5-methyloctadecanate, magnesium 6-methyloctadecanate and calcium 2-hexadecanate.

The anionic sulfates and sulfonates include materials such as sodium tallow alkyl sulfate, triethanolamine alkyl sulfate, and the sodium salt of the condensation of three moles of ethylene oxide plus one mole of a fatty alcohol.

Zwitterionic quaternary ammonium compounds useful herein have the formula:

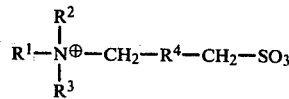

wherein $R_2$ and $R_3$ are each methyl, ethyl, n-propyl, isopropyl, 2-hydroxymethyl or 2-hydroxypropyl, $R_1$ is a 20 to 30 carbon atoms alkyl or alkenyl radical (hereinafter referred to simply as "alkyl") and wherein said alkyl or alkenyl contains from 0 to 2 hydroxyl substituents, from 0 to 5 ether linkages, and from 0 to 1 amide linkage, and $R_4$ is an alkylene group containing from 1 to 4 carbon atoms with from 0 to 1 hydroxyl substituents; particularly preferred are compounds wherein $R_1$ is a carbon chain containing from 20 to 26 carbon atoms selected from the group consisting of alkyls and alkenyls and wherein said alkyls and alkenyls contain 0 to 2 hydroxyl substituents.

Ampholytic compounds useful herein have the formula

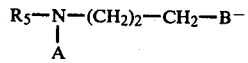

wherein $R_5$ is an alkyl of from 8 to 28 carbon atoms, A is the same as $R_5$ or hydrogen, and B is a water-solubilizing group (particularly $SO_3^-$).

Many additional examples are disclosed in the U.S. Pat. No. 3,743,534, July 3, 1973 to Zamora incorporated herein by reference.

The hair conditioning agent is present on the articles herein in an amount of from about 1.5 grams to about 20.0 grams, preferably about 6.0 grams to about 15.0 grams, per square meter of substrate.

Water Soluble Salt

The articles of the present invention releasably carry, in addition to the hair conditioning agent, a water soluble salt. The useful salts include those which are formed by combining an ion selected from the group consisting of sodium, potassium, ammonium, and magnesium with an ion selected from the group consisting of halogens, sulfate, phosphate, acid phosphate, borate, acetate, bicarbonate, formate and benzoate. Other salts include aluminum hydroxychloride, aluminum sulfate, zirconium oxychloride, zirconium sulfate, zirconyl hydroxychloride, manganese acetate, manganous chloride and manganous sulfate. Preferred salts are the halogen salts of potassium and sodium. Particularly preferred are the chloride salts with sodium chloride being of the most preferred.

The above described salts are used in an amount of from about 0.3 grams to 15.0 grams, preferably from about 1.5 grams to 6.0 grams, per square meter of substrate.

Optional Components

The articles herein can contain, in addition to the salt and hair conditioning agents, any of a number of optional components. Included among such components are perfumes, opacifiers (e.g. titanium dioxide) dyes and hair substantive proteins.

Method of Manufacture

Impregnation or coating the substrate with the hair conditioning agent and/or the water soluble salt is done in any convenient manner, many methods being known in the art. For example, the hair conditioning agent in liquid form can be sprayed onto the substrate.

In another method of making the articles the hair conditioning agent is applied to the substrate by a method generally known as padding. The agent is applied in liquid (melted) form to the substrate from an extrusion device. A roll of substrate is set up on an apparatus so it can unroll freely. As it unrolls, it travels over a slot extruder. Hot molten hair conditioning agent is pumped onto the passing substrate which is then cooled.

In another method the hair conditioning agent, in either a molten form or solution form, is sprayed onto the substrate as it unrolls and any excess agent is then squeezed off by use of squeeze rollers or by a doctor-knife.

Another method of manufacture involves the printing of molten or a solution-form of hair conditioning agent onto the substrate. The level of agent applied is controlled by the proper selection of gravure printing roll. The freshly applied hair conditioning agent is solidified either by a cooling step or a solvent evaporation step.

The water soluble salt can also be applied in any convenient manner known in the art. One method is to dissolve the salt in an aqueous or aqueous/alcoholic solvent and spray the solution onto the hair conditioner treated substrate. Even distribution of the salt is thereby obtained. The same method can be used when the salt is present as a first or bottom coating. Of course when the salt is blended together with the hair conditioning agent the two are applied simultaneously.

The substrates of the articles herein are preferably coated only on one side. This is to provide for a space where the user can place her/his hand without touching the hair conditioning agent. Coating on both sides of the substrate, is, however, within the scope of the present invention.

The resultant treated substrate is flexible. Sheet articles are manufactured from the treated substrate. The treated substrate is optionally slitted at any convenient time during the manufacturing process and packaged as sheets or in rolls. Such articles are of any shape or size, but preferably are rectangular or square in shape and range in size form 7 cm×10 cm to 50 cm×80 cm. It should be understood other shapes are intended to be covered and depend only upon the preferences of the consumer. For example, oval shaped articles as well as articles fabricated to fit over the hand for easier application are feasible.

Industrial Applicability

The hair conditioning article above described provides its benefits when rubbed against the hair of the user. The rubbing transfers the normally solid conditioning agent and the water soluble salt from the substrate to the hair. The amount and point of placement of the agent on the hair is controlled by the user. Thus, the ends of the hair can be treated with a greater amount of conditioning agent than is applied to the roots of the hair. This allows for better hair conditioning and ease-of-combing benefits.

The article can be used in conjunction with the treatment of dry hair. Preferably, however, the article is used on hair which has just been shampooed and partially dried. The delivery of benefits above described is more easily accomplished when the hair is wet. After conditioning the hair in the above manner, the hair is dried in the normal fashion.

It will be recognized the method of conditioning hair above described offers substantial benefits over the more conventional use of liquid hair rinses. Convenience benefits alone are substantial; no additional rinse applications (which can be messy) and fresh water rinse-aways are needed. Performance benefits are also substantial. The proper amount of conditioning agent is better controlled by using the method of this invention as well as its area of placement on the hair. Thus, the consumer can apply a level of conditioning agent by feel and appearance to portions of the hair needing it, i.e. usually near the ends of the hair where tangling problems and lack of desirable levels of sebum occur.

The following examples are illustrative of the invention hereindescribed but are not limiting thereof.

EXAMPLE I

A length of rayon, nonwoven substrate (44 gram basis weight) was removed from a roll and cut into 20.32 cm×22.86 cm sheets. These sheets were equilibrated at 75° F./50% R.H. and weighed. The sheets were then mounted on a flat rack which was tilted into a vertical position and placed in a fume hood. A spray mix was prepared by blending 9 grams of NaCl, 45 grams ethanol (SDA40), and 46 grams distilled water. This mixture was placed in the reservoir of a Supelco TLC spraying device* and a part of it sprayed onto the surface of each sheet. The spray time was adjusted so that 0.14 gram of NaCl was deposited on each sheet (3 grams/square meter of substrate). This was determined by re-equilibrating the sheets at 75° F./50% R.H. and weighing. A second batch, the hair conditioner spray mix, was prepared by mixing 25 grams of di(hydrogenated tallow) dimethyl ammonium chloride (DTDMAC) with 75 grams ethanol. This was sprayed onto the previously coated sheets for a time necessary to deposit 0.76 gram of DTDMAC (16.4 g/square meter of substrate). This quantity was also determined by weighing after equilibration at 75° F./50% R.H.

*This layer chromatography sprayer supplied by Supelco Corp. of Bellefonte, Pennsylvania.

A similar composition was prepared for controlled experiment purposes, in which the article was prepared identically to the above except no NaCl spray mix was employed. The amount of DTDMAC deposited was 0.77 gram (16.4 g/square meter of substrate).

EXAMPLES II–VI

In the following Examples, articles similar to that described in Example I are prepared. The preparation method of Example I is followed.

| Variable | Example | | | | |
|---|---|---|---|---|---|
| | II | III | IV | V | VI |
| Halogen Salt | NaCl | NaCl | KCl | NaCl | → |
| Halogen Salt Level g/m² | 9 | 6 | 3 | → | → |
| Hair conditioning agent | DTDMAC | → | → | → | Adogen 477* |
| Hair Conditioning level g/m² | 16.4 | 16 | 16.4 | 6 | 15 |

*Adogen 477 is N-tallow pentamethylpropane diammonium dichloride supplied by Ashland Chemical Company.

The articles described above when used to condition hair leave wet hair with a less greasy feel and dry hair more manageable.

What is claimed is:

1. An article especially designed for conditioning hair comprising:
   a flexible substrate having a releasable first coating of from about 0.3 gram to about 15.0 grams per square meter of substrate of a water soluble salt selected from the group consisting of
   (A) a salt formed by combining a cation selected from the group consisting of sodium, potassium, ammonium, and magnesium with an anion selected from the group consisting of halogens, sulfate, phosphate, acid phosphate, borate, acetate, bicarbonate, formate and benzoate;
   (B) an aluminum salt selected from the group consisting of aluminum hydroxy chloride and aluminum sulfate;
   (C) a zirconium salt selected from the group consisting of zirconium oxychloride, zirconium sulfate and zirconyl hydroxychloride;
   (D) a manganese salt selected from the group consisting of manganese acetate, manganeous chloride and manganous sulfate; and
   (E) mixtures thereof;
   and as a releasable second coating of from about 1.5 grams to about 20.0 grams per square meter of substrate of a normally solid hair conditioning agent.

2. The article of claim 1 wherein the flexible substrate is selected from the group consisting of paper, woven cloth and non-woven cloth.

3. The article of claim 2 wherein from about 6.0 grams to 15.0 grams of the hair conditioning agent per square meter of flexible substrate is present on the article.

4. The article of claim 3 wherein from 1.5 grams to 6.0 grams of the water soluble salt per square meter of flexible substrate is present on the article.

5. The article of claim 3 wherein the flexible substrate is a non-woven cloth.

6. The article of claim 5 wherein the flexible substrate ranges in size from about 7×10 centimeters to 50×80 centimeters.

7. The article of claim 6 wherein the hair conditioning agent is a quaternary ammonium salt.

8. The article of claim 7 wherein the water soluble salt is selected from the group consisting of potassium chloride and sodium chloride.

9. The article of claim 8 wherein the water soluble salt is sodium chloride and the hair conditioning agent is ditallow dimethyl ammonium chloride.

10. A method of conditioning hair comprising:
rubbing the hair with an article comprised of a flexible substrate having a releasable first coating of from about 0.3 grams to about 15.0 grams per square meter of substrate of a water soluble salt selected from the group consisting of
(A) a salt formed by combining a cation selected from the group consisting of sodium, potassium, ammonium, and magnesium with an anion selected from the group consisting of halogens, sulfate, phosphate, acid phosphate, borate, acetate, bicarbonate, formate and benzoate;
(B) an aluminum salt selected from the group consisting of aluminum hydroxy chloride and aluminum sulfate;
(C) a zirconium salt selected from the group consisting of zirconium oxychloride, zirconium sulfate and zirconyl hydroxychloride;
(D) a manganese salt selected from the group consisting of manganese acetate, manganous chloride and manganous sulfate; and
(E) mixtures thereof;
and as a releasable second coating of from about 1.5 grams to about 20.0 grams per square meter of substrate of a normally solid hair conditioning agent.

11. The method of claim 10 wherein the flexible substrate is selected from the group consisting of paper, woven cloth and non-woven cloth.

12. The method of claim 11 wherein from about 6.0 grams to 15.0 grams of hair conditioning agent per square meter of flexible substrate is present on the article.

13. The method of claim 12 wherein from about 1.5 grams to 6.0 grams of the water soluble salt per square meter of flexible substrate is present on the article.

14. The method of claim 13 wherein the flexible substrate is a non-woven cloth and ranges in size from about 7 to 10 centimeters to 50×80 centimeters.

15. The method of claim 14 wherein the hair conditioning agent is a quaternary ammonium salt.

16. The method of claim 15 wherein the water soluble salt is selected from the group consisting of sodium chloride and potassium chloride.

17. The method of claim 16 wherein the hair conditioning agent is ditallow dimethyl ammonium chloride and the water soluble salt is sodium chloride.

18. The method of claim 10 wherein the hair is wetted prior to being rubbed with the hair conditioning article.

* * * * *